United States Patent
Martens et al.

(10) Patent No.: US 9,945,827 B2
(45) Date of Patent: Apr. 17, 2018

(54) METHOD FOR TESTING A GAS SENSOR IN A GAS-MEASURING SYSTEM

(71) Applicant: Dräger Safety AG & Co. KGaA, Lübeck (DE)

(72) Inventors: Matthias Martens, Groß Schenkenberg (DE); Hans-Ullrich Hansmann, Barnitz (DE); Karsten Hiltawsky, Stockelsdorf (DE); Kai Einecke, Berkenthin (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 0 days.

(21) Appl. No.: 15/358,572

(22) Filed: Nov. 22, 2016

(65) Prior Publication Data
US 2017/0146501 A1 May 25, 2017

(30) Foreign Application Priority Data
Nov. 25, 2015 (DE) .................. 10 2015 015 152

(51) Int. Cl.
*G01N 33/00* (2006.01)
*G01N 33/497* (2006.01)

(52) U.S. Cl.
CPC ....... *G01N 33/007* (2013.01); *G01N 33/0073* (2013.01); *G01N 33/497* (2013.01); *G01N 2033/0072* (2013.01)

(58) Field of Classification Search
CPC ............. G01N 33/007; G01N 33/0073; G01N 2033/0072
See application file for complete search history.

(56) References Cited

U.S. PATENT DOCUMENTS

| | | | |
|---|---|---|---|
| 4,151,739 A | 5/1979 | Breuer et al. | |
| 5,804,695 A * | 9/1998 | Dageforde | G01N 33/0031 73/1.07 |
| 6,182,497 B1 | 2/2001 | Krajci | |
| 6,277,268 B1 * | 8/2001 | Khesin | G01N 27/407 204/424 |
| 7,406,854 B2 | 8/2008 | Lange et al. | |
| 7,645,376 B2 | 1/2010 | Bouchy et al. | |
| 2010/0149538 A1* | 6/2010 | Fleischer | G01N 21/05 356/437 |
| 2014/0331737 A1* | 11/2014 | Kaneblei | G01N 33/0006 73/1.06 |
| 2016/0033446 A1* | 2/2016 | McGuinness | B01F 13/0818 205/793 |

FOREIGN PATENT DOCUMENTS

| | | |
|---|---|---|
| CH | 624 488 A5 | 7/1981 |
| DE | 10 2005 045 272 B4 | 10/2007 |
| WO | 99/17110 A1 | 4/1999 |
| WO | 2007/087403 A2 | 8/2007 |

* cited by examiner

*Primary Examiner* — Ajay Ojha
(74) *Attorney, Agent, or Firm* — McGlew and Tuttle, P.C.

(57) ABSTRACT

A method for testing a gas sensor is based on a gas-measuring system with a test gas source and with a pumping device. A predefined quantity of a gas or of a gas mixture is fed in, from the test gas source, to the gas sensor over a predefined time and metered. The response of a measured signal of the gas sensor is determined as a sensor response. Characteristic variables, from which an indicator of the ability of the gas sensor to operate is determined, are determined from the sensor response.

22 Claims, 2 Drawing Sheets

METHOD FOR TESTING A GAS SENSOR IN A GAS-MEASURING SYSTEM

CROSS REFERENCE TO RELATED APPLICATIONS

This application claims the benefit of priority under 35 U.S.C. § 119 of German Application 10 2015 015 152.5 filed Nov. 25, 2015, the entire contents of which are incorporated herein by reference.

FIELD OF THE INVENTION

The present invention pertains to a method with a gas-measuring system with a gas-measuring device and with a pumping device.

BACKGROUND OF THE INVENTION

Gas-measuring systems and gas-measuring devices are used for industrial gas measurement and to protect persons who are present in areas or rooms from hazards to health and life. In an industrial environment, such as the petrochemical industry, refineries, chemical industry, industrial gas measurement is significant for monitoring explosive or toxic gases or vapors. Both mobile and stationary devices are used. Combinations of mobile or stationary devices are also used to make it possible to perform measurements of gas concentrations or gas analyses in storage tanks, boreholes or silos. Thus, a combination of a mobile gas-measuring device with a charging station for supplying electrical energy as well as with a pump is known from DE 10 2005 045 272 B4. It is thus possible to also use mobile gas-measuring devices for measuring gas concentrations in a drawing shaft or in a borehole by the gas concentration being able to be fed by means of the pump via a long flexible tube from the borehole to the surface to the mobile gas-measuring device. The control of the pump with the start of feeding, the flow rate and further operating properties of the pump is performed by the mobile gas-measuring device or the control thereof. Such a combination of devices is well suited for a temporary, mobile use. Drawbacks arise for continuous use in terms of a continuous power supply. In addition, integration in a data network for forwarding measured values and alarms is relatively complicated, because this would basically have to be performed or configured anew for each temporary mobile use. Also, only a wireless variant could meaningfully be used as a data network in such a configuration, because the necessary network infrastructure is not present for the combination of gas-measuring devices and pump in each industrial plant.

Stationary gas-measuring devices are often and usually distributed as a plurality of sensor units for gas measurement over a plurality of rooms or larger areas in industrial plants. U.S. Pat. No. 6,182,497 B1 describes a gas-measuring system, which is configured to connect a plurality of sensors to a central analysis unit. The sensors may be connected via a universal serial bus (USB).

A gas sensor with an adapter is known from U.S. Pat. No. 7,406,854 B2. The adapter is configured for connecting a flexible tube. It is possible via this flexible tube to bring gas from a remotely located measurement location or a measuring gas or a calibrating gas to the gas sensor. Measuring gas or calibrating gas can thus be fed, for example, by means of a feed pump.

Gas-measuring systems comprising a gas sensor and a gas generator are known from WO 199 917 110 A1 as well as U.S. Pat. No. 7,645,376. Such combinations of gas generators and gas sensors make it possible to test the measuring properties of the gas sensors, especially to determine whether the gas sensor responds sensitively to the admission of a predefined measuring gas concentration.

There is a need, especially for already existing plants or installations of gas-measuring systems, to test the ability of the gas sensors to operate during the operation. In particular, there is a need to be able to test the gas sensors without removing or disassembling the gas sensors at the particular measurement location, which is necessary in the plant.

SUMMARY OF THE INVENTION

Therefore, in the knowledge of the above-described state of the art and analysis of the drawbacks of the state of the art, a basic object of the present invention is to provide a method for testing gas sensors by means of a test gas source for a gas-measuring system.

Another object of the present invention is to provide a method and system for testing gas sensors for a gas-measuring system with a pumping device by means of a test gas source, which method makes it possible to detect changes in operating properties of the gas sensors.

Another object of the present invention is to provide a method and system for testing gas sensors by means of a test gas source for a gas-measuring system with a pumping device, which makes it possible to take into account detected changes in the operating properties of the gas sensors during a subsequent operation of the gas sensors and/or of the gas-measuring system.

According to the invention, a method is provided for testing a gas sensor in a gas-measuring system and/or for testing the gas-measuring system. The method comprises providing the gas-measuring system, which comprises the gas sensor, a control unit, a pumping device and a test gas source. An indicator of readiness of the gas sensor in the gas-measuring system and/or of readiness of the gas-measuring system to operate is determined by the control unit from sequence of the operating states including a first operating state and a sequence of additional operating states. The control unit coordinates the sequence of the operating states including:

continuously feeding a predefined quantity of a gas or of a gas mixture, with the pumping device, from a measuring environment to the gas sensor in the first operating state with a continuous measuring operation;

reducing the quantity of gas fed by the pumping device to the gas sensor in a second operating state;

activating the test gas source in a third operating state;

increasing the quantity of gas fed by the pumping device to the gas sensor in the third operating state;

deactivating the test gas source, after the end of the predefined time, in a fourth operating state;

determining, by measurement, the gas being fed to the gas sensor by the pumping device in the fourth operating state and recoding a set of measured values over a time period;

determining at least one characteristic variable from the set of measured values in the fourth operating state;

determining the indicator of readiness of the gas sensor in the gas-measuring system and/or of the gas-measuring system from the at least one characteristic variable in the fourth operating state; and resuming the first operating state, with continuous measuring operation with continuous feeding of the predefined quantity of gas or gas mixture from the measuring environment through the pumping device, from the fourth operating state.

The present invention is based on the idea of operating, testing, controlling or regulating a test gas source associated with or arranged at a gas sensor in a gas-measuring system such as to detect the ability of the gas sensor to operate. A pumping device is arranged in the gas-measuring system for feeding gas to be analyzed (gas to be measured) from a measuring environment or a measuring location to the gas sensor. Such a test gas source is connected to a gas inlet of the gas sensor such that a test gas, which is determined by measurement at the gas sensor, can flow from the test gas source to the gas sensor.

Suitable test gas sources are, for example, gas generators or configurations of tank-type containers combined with valves or switching means, which are operated, tested, controlled or regulated with a pumping device associated with or arranged at the test gas source such that defined quantities of a test gas provided from the test gas source can be fed to the gas sensor for time intervals whose start and end are defined.

Some of the terms used within the framework of this patent application will be explained at first.

A control signal is defined in the sense of the present invention as an individual control signal, a control signal as part of a set of control signals, as well as a plurality or a set of control signals. A data signal is defined in the sense of the present invention as an individual data signal, a data signal as part of a set of data signals, as well as a plurality or a set of data signals. An output signal is defined in the sense of the present invention as an individual output signal, an output signal as part of a set of output signals, as well as a plurality or a set of output signals. A data connection is defined in the sense of the present invention as a connection of at least two participants by means of a wired, wireless or optical connection, which is suitable for the transmission of control signals, data signals or output signals. Both direct physical connections (cable connections, radio connections, optical light guide connections) and indirect or logic links for transmitting information, control signals, data signals or output signals with physical or data technical conversions or transformations of signals, voltages, currents are also covered.

A test gas is defined in the sense of the present invention as a gas or a gas mixture that is such that the gas sensor of the gas-measuring device is sensitive to a change in the gas concentration of this gas or gas mixture and responds to changes in the gas concentration of this test gas with changes in the gas concentration measured values.

A resetting gas is defined in the sense of the present invention as a gas or gas mixture that is such that the gas sensor of the gas-measuring device is sensitive to a change in a gas concentration of this gas or gas mixture and does not respond to changes in the gas concentration of this resetting gas with changes in the gas concentration measured value.

A gas to be measured is defined in the sense of the present invention as a gas or gas mixture that is such that the gas sensor of the gas-measuring device is sensitive to a change in a gas concentration of this gas to be measured and responds to changes in the gas concentration of this gas to be measured with changes in the gas concentration measured value.

The control unit is configured for carrying out the method according to the present invention for testing a gas sensor in a gas-measuring system. The control unit is usually configured as a programmable or memory-programmable unit configured for programming, for example, in the form of a microprocessor (μP), microcomputer, microcontroller (μC) or in a comparable form of a memory-programmable controller (MPC) or of a programmable logical unit (ASIC, FPGA, PAL, GAL). The control unit may be arranged in the sense of the present invention in or at the test gas source, in or at the gas sensor or as part of an external control or analysis system or arranged as part of an external control or analysis system or associated with the external control or analysis system. The control unit has data storage elements and data supply, which are usually configured in the form of volatile or nonvolatile memory units (RAM, ROM, EEPROM) or removable data storage media (SD card, CF card, USB stick). Furthermore, the control unit has at least one interface, for example, for connection to the external control or analysis system or to the gas sensor, as well as additional and optional interfaces for connection to additional devices or components.

The method according to the present invention for testing a gas sensor in a gas-measuring system and/or for testing the gas-measuring system can be represented as a sequence of steps, which is coordinated by means of the control unit. This sequence of steps starts from a first operating state with a continuous measuring operation, in which a predefined quantity of a gas or of a gas mixture is continuously fed by the pumping device from the measuring environment to the gas sensor. In the method according to the present invention for testing a gas sensor in a gas-measuring system and/or for testing the gas-measuring system, the control unit performs the following operations in the following sequence of steps:

a quantity of gas fed by the pumping device to the gas sensor is reduced in a second operating state, the test gas source is activated at an activation time (tactivate) in a third operating state, the quantity of gas being fed by the pumping device to the gas sensor is increased for a predefined time in the third operating state, the test gas source is deactivated at a deactivation time (tdeactivate) in a fourth operating state after the end of the predefined time, the gas being fed to the gas sensor is detected by the gas sensor by measurement in the fourth operating state and is recorded as a set of measured values over a time period, at least one characteristic variable is determined from the set of measured values in the fourth operating state, an indicator of readiness of the gas sensor in the gas-measuring system and/or of the gas-measuring system to operate is determined from the at least one characteristic variable in the fourth operating state, the first operating state with continuous measuring operation with continuous feeding of the predefined quantity of gas or gas mixture from the measuring environment by the pumping device is resumed from the fourth operating state.

The predefined quantity of gas or gas mixture continuously fed in the first operating state is embodied, for example, as a flow rate in the form of a mass flow $\dot{m}$, or volume flow $\dot{V}$, or by means of a predefined flow velocity V.

In the second operating state, the gas sensor is brought into a state in which no gas, either gas to be measured from the measuring environment or test gas from the test gas source is fed to the gas sensor and a change in the measured value cannot thus be induced, either. Thus, this quasi represents an initialization, with which a reference point is set for the subsequent measured values of the gas sensor.

A predefined quantity of gas or gas mixture $\dot{V}_{generate}$ with known gas concentration $c_{generate}$ is fed as a bolus to the gas sensor or quasi metered in the third operating state after or on activation of the test gas source at an activation time $t_{activate}$ for a predefined time $t_{generate}$ until a deactivation of the test gas source at a deactivation time $t_{deactivate}$ in the fourth operating state. This bolus of gas brings about a reaction in the gas sensor.

If the gas sensor is configured, for example, as an electrochemical gas sensor and the metered bolus is a bolus of a test gas, a change will occur in the measured value based on a chemical and/or electrochemical reaction. If the gas sensor is configured, for example, as an optical gas sensor with a measuring cuvette and the metered bolus is a bolus of a test gas, an attenuation of the propagation of light in the measuring cuvette, a change in the measured value, will occur in a wavelength range of the optical gas sensor due to the absorption properties of the test gas. If the gas sensor is configured, for example, as a catalytic gas sensor and the metered bolus is a bolus of a test gas, there will be a change in the measured value based on combustion reactions and/or chemical reactions taking place at the measuring element (pellistor) of the catalytic gas sensor with the test gas.

The measured values of the gas sensor as well as changes in the measured values of the gas sensor are determined by measurement in the fourth operating state and plotted as a set of measured values over a time course, for example, as a curve or curve course. Such a typical course of the curve as a reaction to the introduction of a bolus is called sensor response $t_{response}$ and can be divided in time into three essential phases:

A phase during which the measured values rise with a great change in the amplitude ΔA of the measured value over a time difference Δt, wherein an average gradient of rise ΔA/Δt with positive sign is obtained, for example, by means of a linear approximation, A measured value plateau phase with a slight change in the amplitude ΔA of the measured value over a time difference Δt, wherein an average amplitude $A_{Average}$ is obtained, for example, by means of a linear approximation. This measured value plateau phase typically has a peak of the amplitude $A_{peak}$, which represents the maximum response of the gas sensor to the introduction of the bolus.

A phase during which the measured value falls, during which the response of the gas sensor fades out with a great change in the amplitude ΔA of the measured value over a time difference Δt, wherein an average gradient of fall ΔA/Δt with negative sign is obtained, for example, by means of a linear approximation.

The first operating state is resumed from the fourth operating state after the end of the sensor response.

In a preferred embodiment, a set of messages, which are provided by the output unit, is generated by means of the control unit or an output unit connected to the control unit in a fifth operating state or in an additional operating state before, after or on resumption of the continuous measuring operation with continuous feeding of the predefined quantity of gas through the pumping device on the basis of the indicator of readiness of the gas sensor to operate. Such messages on the basis of the indicator of readiness to operate may also be provided or outputted by the output unit in the form of state messages, error messages, notes, warnings, instructions for maintenance or replacement or also in the form of optical, acoustic or visual alarms to a user.

Such messages, such as state messages, error messages, notes, warnings, instructions for maintenance or replacement, as well as the indicator of readiness to operate, the characteristic variables or the set of measured values itself may also be provided in the fifth or additional operating state in a preferred embodiment by the control unit and/or the output unit to a central analysis system to a data bank system or to a memory on a mobile data storage medium.

In another preferred embodiment, the control unit analyzes in the fourth operating state the set of measured values of the gas sensor and/or the sensor response and divides the sensor response $t_{response}$ into the three phases, namely, the measured value rise phase $t_{rise}$, measured value plateau phase $t_{plateau}$ and measured value fall phase $t_{fall}$.

The start and end of the sensor response can typically be determined from the signal curve such that a time $t_{start}$, at which the current amplitude $A_{start}$ of the measured value has reached a value of 10% of the peak amplitude $A_{peak}$ of the average amplitude $A_{average}$ is selected as the start of the rise time and a time $t_{end}$ at which the sensor response has declined to such an extent that the current amplitude $A_{end}$ of the measured value has dropped again to a value of 10% of the peak amplitude $A_{peak}$ or the average amplitude $A_{average}$ is selected as the end of the fall time.

The time difference between the time $t_{end}$ and the time $t_{start}$ forms the duration of the sensor response $t_{response}=t_{end}-t_{start}$.

The application of the so-called rise time $t_{10-90}$ commonly used in measuring technique is suitable for the definition of the duration of the measured value rise phase; this corresponds to the duration during which the amplitude of the measured values has values in a value range between 10% and 90% of the peak amplitude $A_{peak}$ or of the average amplitude $A_{average}$ during the measured value rise phase.

Table 1 below shows what states or properties can be analyzed by the control unit, partly compared with a comparison variable, as characteristic variables in the individual phases of the sensor response from the time curve of the measured values of the gas sensor in the individual phases of the sensor response, and what conclusions and consequences arise for the characterization of the readiness to operate and/or for the analysis of the state as a possible indicator or as indicators of the ability of the gas sensor as well as of the gas-measuring system with gas sensor to operate. Suitable comparison variables are available for comparison, for example, in the form of comparison values, which are stored in the elements associated with the control unit for data storage and data supply (memory) and which are provided from measured values or time curves of the measured values from preceding measurements, especially at the times of start-up, adjustment, initialization or other tests of the gas sensor.

Table 1 shows, in addition, what messages can be outputted in a preferred embodiment for a user by means of an output unit connected to the control unit in the form of notes, warnings or alarms on the basis of the characteristic variable as a characterization of the readiness to operate and/or analysis of the state.

TABLE 1

| Measured variable/ Characteristic variable | Analyzed property of the measured variable | Expected or predefined comparison variables | State of sensor | Message |
|---|---|---|---|---|
| Integral of the measured signal of the gas sensor (sensor response) | Integral $\int A(t)\,dt >$ comparison variable | Measured signal integral $\int A(t)\,dt_{desired}$ | a) Sensitivity too high<br>b) Zero point shifted<br>d) Test gas source defective | a) Warning: Sensitivity is increased<br>b) Note: Zero point is shifted<br>d) Warning: Check test gas source |
| Integral of the measured signal of the gas sensor (sensor response) | Integral $\int A(t)\,dt <$ comparison variable | Measured signal integral $\int A(t)\,dt_{desired}$ | a) Sensitivity is reduced<br>b) Zero point is shifted<br>c) Test gas source defective<br>d) Leaks | a) Warning: Sensitivity is reduced<br>b) Note: Zero point is shifted<br>c) Warning: Check test gas source<br>d) Note: Perform leak test |
| Response time of gas sensor ($t_{response}$) | Response time $t_{response} >$ comparison variable | Duration of activation of the test gas source ($t_{activate}-t_{deactivate}$)a) | a) Leaks in the system<br>b) Test gas source defective | a) Alarm: Risk of dilution of gas to be measured<br>a) Note: Perform leak test<br>a) Note: Check pneumatic system<br>b) Warning: Check test gas source |
| Gradient of rise of the gas sensor ($\Delta A/\Delta t$) (sensor response) | Gradient of rise ($\Delta A/\Delta t$) > comparison variable | Desired gradient of rise ($\Delta A/\Delta t$)$_{desired}$ | a) Changes in the sensory properties (e.g., conversion of substance)<br>b) Leaks<br>c) Changes in the flow arriving at the gas sensor<br>d) Test gas source defective | a) Alarm Replacement of sensor<br>b) Note: Perform leak test<br>c) Note: Check pneumatic system<br>d) Warning: Check test gas source |
| Average amplitude $A_{average}$ of the gas sensor (sensor response) to the test gas bolus | Average amplitude $A_{average} <$ comparison variable | Average desired amplitude $A_{average\_desired}$ | a) Sensitivity too low<br>b) Zero point shifted<br>c) Leaks<br>d) Test gas source defective | Warning:<br>a) Sensitivity is reduced<br>b) Note: Zero point is shifted<br>c) Note: Perform leak test<br>d) Warning: Check test gas source |
| Peak amplitude $A_{peak}$ of the gas sensor (sensor response) to the test gas bolus | Peak amplitude $A_{peak} <$ comparison variable | Peak desired amplitude $A_{peak\_desired}$ | a) Changes in the measuring properties of the sensor | a) Alarm: Replacement of sensor |
| Time curve of the measured signal of the gas sensor (sensor response) to the test gas bolus | Duration of the sensor response ($t_{rise}$) > comparison variable | Sensor response ($t_{rise\_desired}$) | a) Changes in the measuring properties of the sensor<br>b) Quantity of test gas too small | a) Alarm: Replacement of sensor<br>c) Note: Check pneumatic system |
| Time curve of the measured signal of the gas sensor (sensor response) to the test gas bolus | Duration of the sensor response $T_{rise} <$ comparison variable | Sensor response ($t_{rise\_desired}$) | a) Changes in the measuring properties of the sensor<br>b) Quantity of test gas too large | a) Alarm: Replacement of sensor<br>c) Note: Check pneumatic system |

Further preferred embodiments of the method for testing the gas sensor and for characterizing the readiness of the gas sensor to operate arise from a state analysis listed in Table 1, on the basis of signals of the gas sensor.

Furthermore, further preferred embodiments arise from Table 1, in addition to analyses of the state of the gas sensor, for testing the readiness of the pumping device or of the pneumatic system, with feed lines, connection elements, switch-off elements, for example, valves, to operate and for characterizing the readiness of the pumping device to operate.

In a preferred embodiment, the peak value of the amplitude $A_{peak}$ of the measured signal of the gas sensor is analyzed by the control unit in the fourth operating state compared to the peak desired amplitude $A_{peak\_desired}$ as a comparison variable in order to determine the at least one characteristic variable for determining the indicator of readiness of the gas sensor to operate in the gas-measuring system and/or of the gas-measuring system.

In another preferred embodiment, the average amplitude $A_{average}$ of the measured signal of the gas sensor is analyzed by the control unit as a comparison variable in the fourth operating state in order to determine the at least one characteristic variable for determining the indicator of readiness of the gas sensor in the gas-measuring system, and/or of the gas-measuring system to operate.

In another preferred embodiment, the duration of the rise time of the sensor response $t_{rise}$ of the measured signal of the gas sensor is analyzed by the control unit compared to the expected duration of the rise time of the sensor response $t_{rise\_desired}$ as a comparison variable in order to determine the at least one characteristic variable for determining the indicator of readiness of the gas sensor in the gas-measuring system and/or of the gas-measuring system to operate. The duration of the sensor response $t_{rise}$ is determined by the control unit on the basis of determined values of the rise phase of the measured value, especially from the signal curve after activation of the test gas source.

In another preferred embodiment, the gradient of rise ($\Delta A/\Delta t$) of the measured signal of the gas sensor is analyzed in the fourth operating state as a change in the amplitude A of the measured value as a function of the time difference $\Delta t$ compared to the expected desired gradient of rise ($\Delta A/\Delta t)_{desired}$ as a comparison variable in order to determine the at least one characteristic variable for determining the indicator of readiness of the gas sensor in the gas-measuring system and/or of the gas-measuring system to operate. The gradient of rise of the sensor response ($\Delta A/\Delta t$) is determined by the control unit on the basis of determined values of the rise phase of the measured value, especially from the signal curve after activation of the test gas source.

In another preferred embodiment, an integral of the amplitude $\int A(t) dt$ of the measured signal of the response of the gas sensor over the rise phase of the measured value, the measured value plateau phase and the fall phase of the measured value is analyzed in the fourth operating state compared to a predefined measured signal integral $\int A(t) dt\_{desired}$ as a comparison variable in order to determine the at least one characteristic variable for determining the indicator of readiness of the gas sensor in the gas-measuring system and/or of the gas-measuring system to operate.

In another preferred embodiment, the duration of the sensor response $t_{response}$ of the measured signal of the gas sensor compared to the activation time of the test gas source ($t_{activate}-t_{deactivate}$) is analyzed in the fourth operating state as a comparison variable in order to determine the at least one characteristic variable for determining the indicator of readiness of the gas sensor in the gas-measuring system and/or of the gas-measuring system to operate.

For example, leaks or also blockages in the feed lines, connection elements, switch-off elements can be distinguished in another, especially preferred embodiment from malfunctions of the gas sensor by the control unit by a combined analysis of the different measured variables and/or characteristic variables of the above-described embodiments into and/or with one another being performed.

A combination of at least two of the characteristic variables of the above-described embodiments is preferably analyzed by the control unit in the fourth operating state as a characteristic variable to determine the indicator of readiness of the gas sensor in the gas-measuring system and/or of the gas-measuring system to operate.

From this arises as another advantage of the present invention that a plausibility check is made possible by the fact that responses expected to the introduction of the test gas bolus or predefined responses in the sensor response $t_{response}$ of the gas sensor as desired values ($\int A(t) dt\_{desired}$, $t_{rise\_desired}$, $(\Delta A/\Delta t)\_{desired}$, $A_{average\_desired}$, $A_{peak\_desired}$, $t_{activate}-t_{deactivate}$) combined into one another and/or with one another and with the characteristic variables determined, which are derived by the control unit from the measured values actually determined by measurement, and possible malfunctions of the gas sensor differ from malfunctions of the pumping device or of the pneumatic system or of the gas-measuring system as a whole. For example, especially the gradient of rise ($\Delta A/\Delta t$) of the measured signal of the gas sensor and/or the peak of the amplitude $A_{peak}$ of the measured signal of the gas sensor and/or the average amplitude $A_{average}$ of the measured signal of the gas sensor and/or the duration of the rise time of the sensor response $t_{rise}$ of the measured signal of the gas sensor and/or the integral $\int A(t) dt$ of the amplitude of the measured signal of the sensor response of the measured signal of the gas sensor and/or the duration of the sensor response $t_{response}$ of the measured signal of the gas sensor are preferably analyzed by the control unit combined with one another.

One example of such a plausibility check is that the activation time of the test gas source ($t_{activate}-t_{deactivate}$) cannot last longer in time than the total duration of the sensor response $t_{response}$.

In summary, the fact that the gas sensor can be tested regularly during the ongoing operation is seen as an essential advantage of the present invention. The present invention offers the advantage that the pumping device, which supplies the gas sensor with gas to be analyzed from the measuring environment during the measuring operation, also makes it possible by means of the test gas source to test the gas-measuring system, and/or the gas sensor. As a result, the reliability of the gas-measuring system and/or of the gas sensor is improved as a whole. Furthermore, one advantage of the present invention is that in addition to the testing of the gas sensor, malfunctions of the pumping device or of the pneumatic system can also be detected and different malfunctions can be distinguished from one another.

The present invention will be explained in more detail in a combined description of the figures by means of the following figures and the corresponding descriptions of the figures without limitation of the general idea of the present invention. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
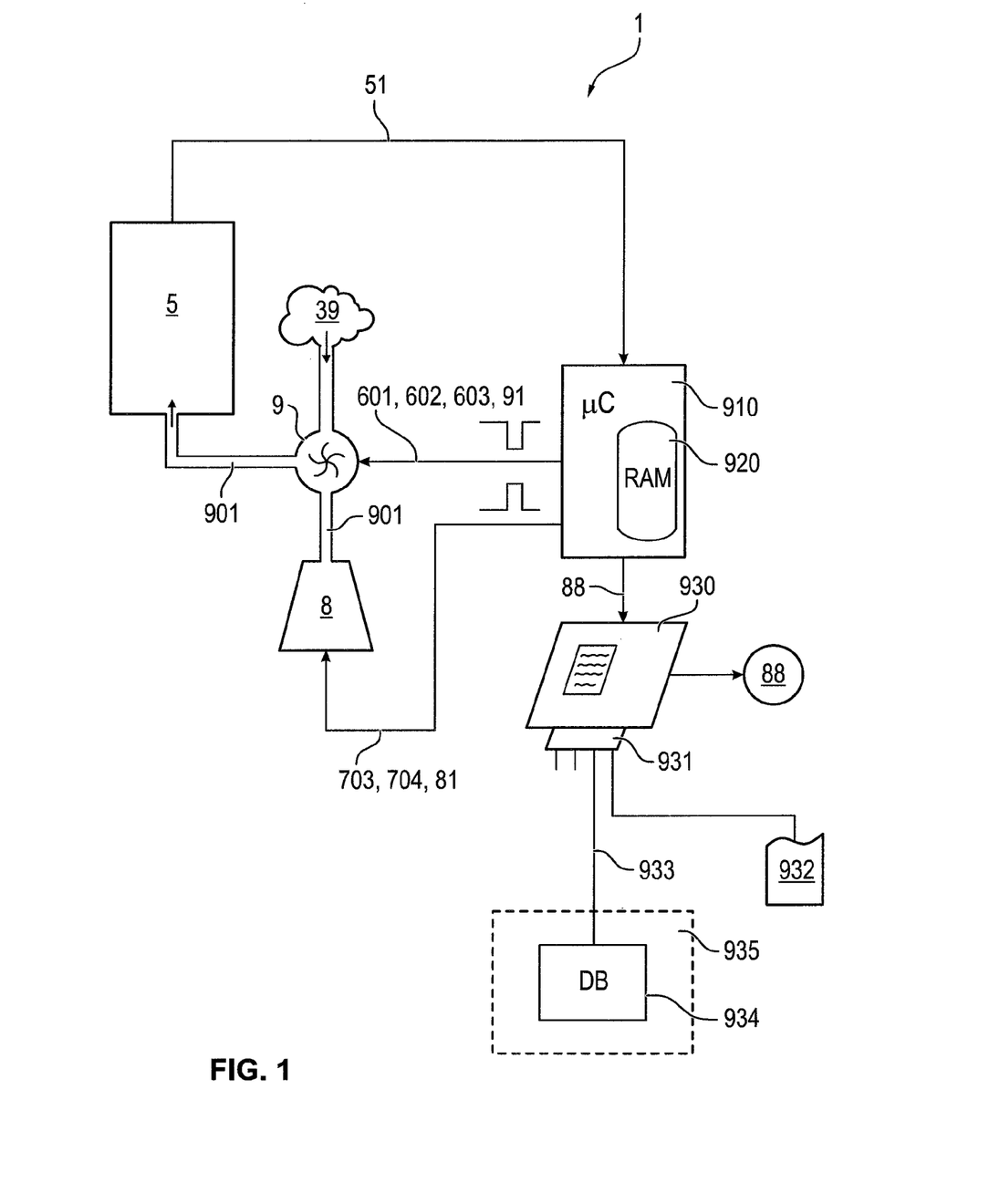
FIG. 1 is a schematically simplified view showing a pumping device with a test gas source and with a gas sensor in a gas-measuring system.

Referring to the drawings, in a schematically simplified view, FIG. 1 shows a gas-measuring system 1 with a pumping device 9, with a test gas source 8 and with a gas sensor 5. A control unit 910 is provided with a memory 920. The control unit 910, generally and in principle, shown as a separate unit in this configuration according to FIG. 1, provides the cooperation with the pumping device 9 and with the gas generator 5. For example, an arrangement in/at the gas sensor 5, in/at the pumping device 9 or in/at a control and analysis system, not shown in this FIG. 1, represent variants of the arrangement of the control unit 910. The control unit 910, comprised of a processor unit (µP, µC), is configured, in conjunction with the memory 920, to implement a procedure 100 (schematically represented in FIG. 2) for testing the gas sensor 5. Further details, related to design, which are necessary for feeding quantities of gas into the gas sensor, for example, gas inlet membrane, flame protection unit, are not shown in this view in FIG. 1 for reasons of clarity.

Electronic components, power supply elements, as well as design details concerning the gas-carrying components, for example, pump, pump motor, valves, temperature, pressure and/or flow sensor systems, are not shown in this schematic view in this FIG. 1 for reasons of clarity.

The details of the configuration of the test gas source 8 with means for activation/deactivation, the species and type of the test gas, the configuration as a gas generator with electrical activation or embodiment variants in the form of a tank-type container in combination with valves, switching means, as well as sensor systems (pressure, temperature, flow) as well as design details of the manner in which the test gases are generated, provided and metered are necessary, are not shown in this schematic view in FIG. 1 for reasons of clarity.

A gas feed system 901, which is shown only schematically in this FIG. 1, connects the test gas source 8, the gas sensor 5 and the pumping device 9 with one another in such a manner that gas or air can optionally be fed from a measuring environment 39 or from the test gas source 8 to the gas sensor 5 by means of the pumping device 9. The control unit 910 controls both the test gas source 8 with activation signals 703, 704, 81 and the pumping device 9 with flow rate control signals 601, 602, 603, 91. In addition, the control unit 910 receives measured signals, time curves of measured signals 51 from the gas sensor 5 as data. An output unit 930, which is configured to display the course 100 (FIG. 2) of the method for testing a gas sensor 5, to display states of the pumping device 9, of the control unit 910, of the test gas source 8 and of the gas sensor, and is also configured to display measured signals, time curves of measured signals 51 of the gas sensor 5 in the form of at least one output signal 88, is optionally connected to the control unit 910.

A data interface 931 configured for the supply 933 of the output signal in the data exchange is optionally connected to this output unit 930.

The pumping device 9 shown in this FIG. 1 with test gas source 8 and with gas sensor 5 is used as an example for embodiment variants and combination possibilities of how such a control unit 910, memory 920, test gas source 8, gas feed system 901, pumping device 9 and gas sensor 5 can be arranged with one another and in relation to one another in series in the gas feed system 901 in order to carry out the method (FIG. 2) for testing the gas sensor 5 in the gas-measuring system 1. Embodiments in which the pumping device 9 is configured as a part of the gas sensor 5 are covered by the inventive idea of testing the gas sensor 5 in the gas-measuring system just as much as are embodiments in which components, such as the memory 920, control unit 910, output unit 930, data output unit 931 are arranged as parts of the gas-measuring system in relation to one another or with one another and cooperate to carry out the method (FIG. 2) for testing the gas sensor 5 in the gas-measuring system.

In addition, the gas feed system 901 may have components in the interior of the pumping device 9, test gas source 8, from or to the gas sensor 5, from the pumping device 9 or from the test gas source 8, as well as feed lines outside the pumping device 9, the test gas source 8 for establishing gas-carrying connections in the gas-measuring system 1. The output unit 930 can provide the result of the testing of the gas-measuring system 1 by means of the optional data interface 931 to the outside in different ways. The data interface 931 may be configured for supply 933 for an optical data transmission (IrDa), for wireless data transmission (WLAN, Bluetooth), and for wired data transmission (Ethernet, LAN, USB, industrial communication bus). Supply 933 is possible, for example, on a mobile memory 932 (memory stick, e.g., CF card, SD card, diskette, USB stick, external hard drive), a supply 933 into a central or non-central data network (LAN, WLAN), preferably configured as a data bank 934, or supply 933 to a central or non-central analysis system 935 in an industrial automation environment is possible as well.

It is possible in this way to make available the results of the testing of the gas-measuring system 1 in order to make it possible to organize maintenance or repair procedures centrally or non-centrally. The output unit 930 may also be configured in this case as a separate mobile unit, by means of which the results of the testing of the gas sensors 5 or of the gas-measuring system 1 can be collected by the maintenance personnel in a mobile form and subsequently made available for a central analysis system, for example, as a data transfer (upload) by means of a data-reading device and a personal PC.

Figure 2:
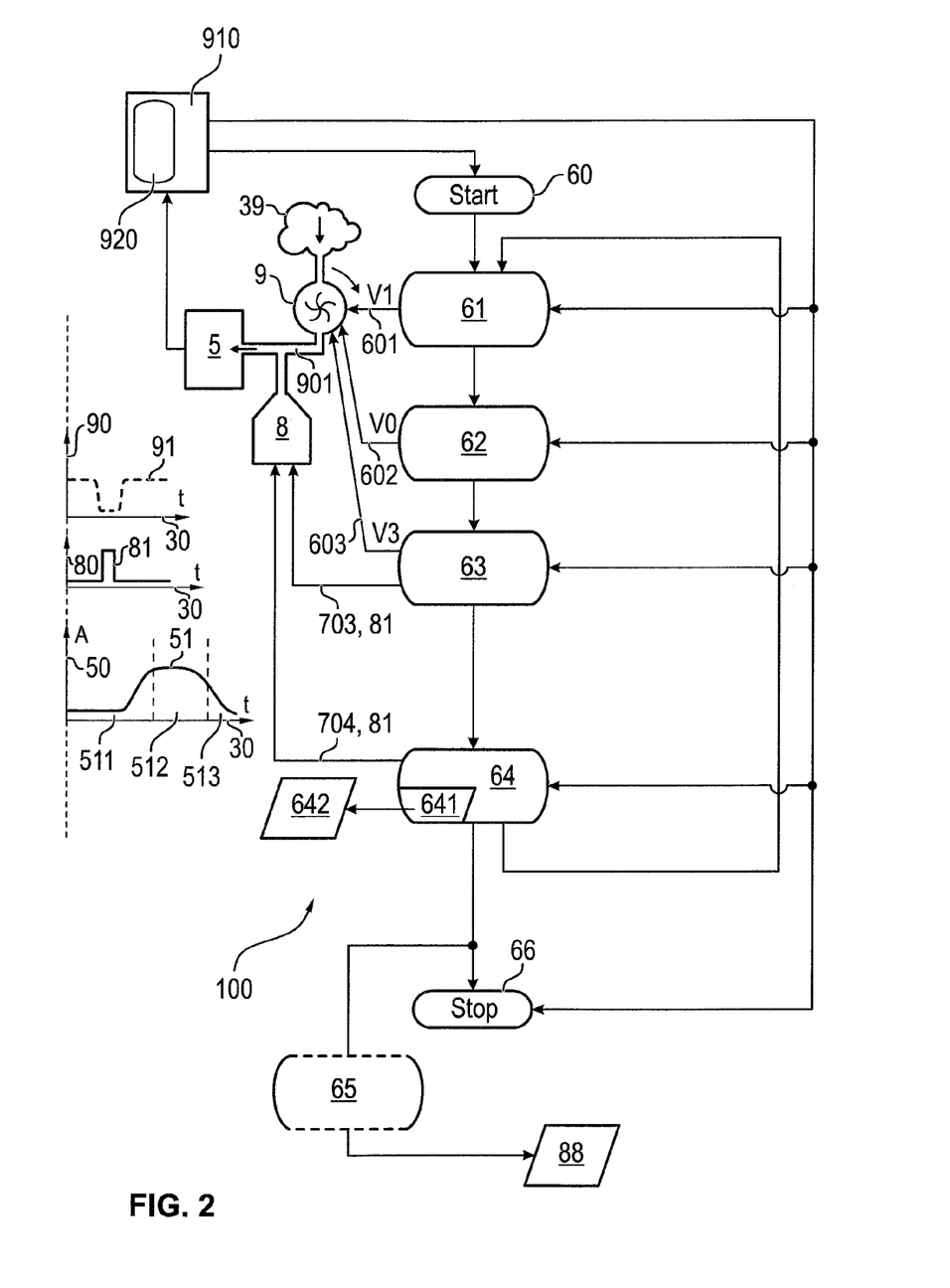
FIG. 2 is a view showing a schematic course of a method for testing a gas sensor with a pumping device and with a test gas source in a gas-measuring system.

FIG. 2 schematically shows a procedure 100 of the method with a start 60 and with an end 66 and with a sequence of steps 61, 62, 63, 64, 65 for testing a gas sensor 5 in a gas-measuring system 1 (FIG. 1) with a control unit 910 and with a memory 920. Identical components in FIG. 1 and FIG. 2 are designated in FIG. 2 by the same reference numbers as in FIG. 1. The control unit 910 comprising e.g., as a processor unit (μP, μC), is configured to, in conjunction with the memory 920, to implement the schematic procedure 100. The schematic procedure 100 starts after a start 60 from a first operating state 61 (step 1) with a continuous measuring operation, in which the pumping device 9 is prompted by means of a first flow rate control signal V1 601 to continuously feed a defined quantity or a defined volume of gas from the measuring environment 39 to the gas sensor 5 via a gas feed line system 901.

In a second operating state 62 (step 2) following the first operating state 61, the pumping device 9 is prompted via a second flow rate control signal V0 602 to reduce the quantity of gas being fed to the gas sensor 5. The quantity of gas is preferably reduced to such an extent that a state without movement of gas or gas supply develops at the gas sensor 5 and the gas sensor thus sends, a measured signal 51 that is used as a type of zero value as a reference point for further and subsequent measurements in the procedure 100 and this measured signal 51 is stored in the memory 920 by means of the control unit 910.

In a third operating state 63 (step 3) following the second operating state 62, the test gas source 8 is activated via an activation signal 703 to release a test gas, and the pumping device 9 is promoted at the same time or subsequently via a third flow rate control signal V3 603 to increase the quantity of gas being fed to the gas sensor 5 to a predefined quantity, so that a test gas generated or provided by the test gas source 8 is thus fed to the gas sensor 5. In a fourth operating state 64 (step 4) following the third operating state 63, the release of the test gas from the test gas source 8 is deactivated by means of a deactivation signal 704. The gas being fed to the gas sensor 5 in the fourth operating state 64 is detected by the control unit 910 by measurement and recorded as a set of measured values or measured signals over a time course.

Furthermore, at least one characteristic variable 641 is determined from the set of measured values in the fourth operating state 64, and an indicator 642 for the readiness of the gas sensor 5 to operate in the gas-measuring system 1 (FIG. 1) and/or of the gas-measuring system (FIG. 1) is determined and provided from the at least one characteristic variable 641. The first operating state 61 with continuous measuring operation with continuous feeding of the predefined quantity of gas from the measuring environment 39 through the pumping device 9 to the gas sensor 5 is subsequently resumed again from the fourth operating state 64.

Three time curves are schematically shown at the left edge of FIG. 2:

An amplitude A 50 of the measured signal 51 of the gas sensor 5 over the course of time t 30, an amplitude 80 of the activation signal 81 of the test gas source 8 over the course of time t 30, and an amplitude 90 of the flow rate of the pumping device 9 over the course of time t 30.

These three time curves 50, 80, 90 show, each synchronized with one another in time, the time curve of the flow rate of the pumping device 9, of the activation of the test gas source 8 and the resulting response in the measured signal of the gas sensor 5 as a so-called sensor response to the influence and control 601, 602, 603, 703, 704 of the pumping device 9 and test gas source 8 by the control unit 910.

Characteristic variables arise during the so-called sensor response, for example, during a phase of rise time 511 of the measured signal from the zero value of the measured signal 51 of the gas sensor 5 until a built-up, approximately stable peak of the measured signal is reached immediately following the activation 703 of the test gas source 8, during a phase 512 (plateau phase) with built-up, approximately stable peak of the measured signal, and during a phase 513 of a fall time of the measured signal from the built-up, approximately stable measured signal (phase 512) to the zero value of the measured signal 51 of the gas sensor 5 following the deactivation 704 of the test gas source.

The list of the characteristic variables 641, from which, for example, the indicator 642 of the readiness of the gas sensor 5 to operate can be determined, and Table 1 with the corresponding explanations to the sensor response are referred to here. Possible responses to the activation of the test gas source 8, characteristic variables 641 belonging to the three phases 511, 512, 513, the gradient of rise ($\Delta A/\Delta t$) of the measured signal 51 of the gas sensor 5, the peak of the amplitude $A_{peak}$ of the measured signal 51 of the gas sensor 5, the average amplitude $A_{average}$ of the measured signal 51 of the gas sensor 5, the duration of rise of the sensor response $t_{rice}$ of the measured signal 51 of the gas sensor 45, and the integral of the sensor response $t_{response}$ of the measured signal 51 of the gas sensor 5 can be found in this Table 1.

The determination of the indicator 642 of the readiness of the gas sensor 5 to operate in the fourth operating state 64 (step 4) is preferably carried out on the basis of a comparison with comparison variables 466, as they are likewise listed in Table 1.

Another possibility of determining the indicator 642 of the readiness of the gas sensor 5 to operate in the fourth operating mode 64 (step 4) arises in a combined analysis of the different measured variables and/or characteristic variables: The gradient of rise ($\Delta A/\Delta t$) of the measured signal 51 of the gas sensor 5, the peak of the amplitude $A_{peak}$ of the measured signal 51 of the gas sensor 5, the average amplitude $A_{average}$ of the measured signal 51 of the gas sensor 5, the duration of rise of the sensor response $t_{rise}$ of the measured signal 51 of the gas sensor 5, the integral $\int A(t)\,dt$ of the amplitude of the measured signal 51 of the gas sensor 5, the duration of the sensor response $t_{response}$ of the measured signal 51 of the gas sensor 5 by the control unit 910.

Another possibility for determining the indicator 642 of the readiness of the gas sensor 5 to operate in the fourth operating state 64 (step 4) is for the control unit 910 to perform certain maneuvers when controlling the pumping device 9, for example, for the test gas source 8 to delay the release of the test gas in the third operating state 63 (step 3) or to activate it with different feed rates, so that different working points of the flow rate can be reached by the pumping device 9 by means of the control unit 910, which makes possible a differentiated diagnosis for determining the indicator 642 of the readiness of the gas sensor 5 to operate. Such maneuvers may also be carried out in programmed cycles. The maneuvers pertain to the pneumatic system and switch the pump in the pumping device 9 to other working points with changed volume flow. A response of the pressure and/or flow sensor system usually necessary for the operation of the pumping device 9 and optionally the response of the gas sensor 5 to the changed volume flow provide information for the correct performance of the maneuver compared to a stored desired response.

An example of such a maneuver is a short-term stop of the pump in the pumping device 9, initiated by the control unit 910. A time constant of the pneumatic system 901 can be determined, a feed volume can be estimated and, by means of a previously determined reference volume stored in the memory 920 (FIG. 1), the location of a leak can be estimated with such a stop maneuver by the control unit 910 from the sensor response.

The indicator 642 of the readiness of the gas sensor 5 to operate can be outputted in an optional, fifth operating state 65 (step 5) of the method in procedure 100 as an output value 88 by means of an output unit 930 (FIG. 1), not shown in this FIG. 2.

While specific embodiments of the invention have been shown and described in detail to illustrate the application of the principles of the invention, it will be understood that the invention may be embodied otherwise without departing from such principles.

APPENDIX

List of Reference Numbers

1 Gas-measuring system
5 Gas sensor
8 Test gas source
9 Pumping device
30 Time t, x axis
39 Environment, measuring environment (air)
50 Amplitude A of the measured signal of the gas sensor 5, y axis
51 Time curve of the measured signal of the gas sensor 5
60 START
61 First operating state/step 1
62 Second operating state/step 2
63 Third operating state/step 3
64 Fourth operating state/step 4
65 Fifth operating state/step 5
66 STOP
80 Activation signal of the test gas source 8, y axis 81 Time curve of the activation signal of the test gas source 8
88 Output value
90 Flow rate of the pumping device 9, y axis
91 Time curve of the flow rate of the pumping device 9
511 Phase of rise time
512 Phase with stable measured signal (plateau)
513 Fall phase time
601 First flow rate control signal V1
602 Second flow rate control signal V0
603 Third flow rate control signal V3
641 Characteristic variable
642 Indicator of readiness of the gas sensor 5 to operate
703 Activation signal for the test gas source
704 Deactivation signal for the test gas source
901 Gas feed line system
910 Control unit
920 Memory
930 Output unit
931 Data interface
932 Mobile memory
933 Supply as a data signal
934 Data bank
935 Analysis system

What is claimed is:

1. A method for testing a gas sensor in a gas-measuring system and/or for testing the gas-measuring system, the method comprising the steps of:
providing the gas-measuring system, comprising the gas sensor, a control unit, a pumping device and a test gas source for providing or generating a known test gas, at a monitoring location to monitor gas of a measuring environment at which the gas-measuring system is situated;
selecting an indicator of readiness for measurement operation of the gas sensor in the gas-measuring system and/or an indicator of readiness for measurement operation of the gas-measuring system by the control unit from sequence of operating states including a first operating state and a sequence of additional operating states;
coordinating, with the control unit, the sequence of the operating states comprising:
continuously feeding a predefined quantity of a gas or of a gas mixture, with the pumping device, from the measuring environment to the gas sensor in the first operating state to provide a continuous environmental gas measuring operation;
reducing the quantity of gas fed by the pumping device from the measuring environment to the gas sensor in a second operating state such that the such that the feed of gas from the measuring environment is terminated;
activating the test gas source in a third operating state to generate or provide the known test gas, with the feed of gas from the measuring environment terminated, in the third operating state;
increasing the quantity of gas fed by the pumping device to the gas sensor in the third operating state to feed the test gas generated or provided by the test gas source to the gas sensor;
deactivating the test gas source, after the end of the predefined time, in a fourth operating state;
determining, by measurement with the gas sensor, the gas being fed to the gas sensor by the pumping device in the fourth operating state and recording a set of measured values over a time period;
determining at least one characteristic variable from the set of measured values in the fourth operating state;
selecting the indicator of readiness for measurement operation of the gas sensor in the gas-measuring system and/or of the gas-measuring system based on the determined at least one characteristic variable in the fourth operating state; and
resuming the first operating state, with continuous measuring operation with continuous feeding of the predefined quantity of gas or gas mixture from the measuring environment through the pumping device, from the fourth operating state, whereby the indicator of readiness for measurement operation is selected and available with the system in the first operating state with ongoing continuous measuring operation.

2. The method in accordance with claim 1, wherein selecting the indicator of readiness for measurement operation of the gas sensor in the gas-measuring system and/or of the gas-measuring system further comprises:
providing saved data comprised of expected predefined comparison variables;
providing saved data comprised of sensor states;
associating each sensor state of the sensor states with one or more of the expected predefined comparison variables;
comparing the determined at least one characteristic variable with one or more of the expected predefined comparison variables; and
selecting, based on the comparison and based on the association, one or more sensor states of the sensor states.

3. The method in accordance with claim 2, further comprising the step of providing a set of messages each associated with one or more of the sensor states, wherein:
selecting one or more sensor states of the sensor states further comprises selecting one or more of the messages;
the set of messages is provided by an output unit and an output of the selected one or more messages is generated by means of the control unit or by means of the output unit connected to the control unit, in a fifth or in an additional operating state, on a basis of the indicator of readiness for measurement operation of the gas sensor, whereby the indicator of readiness for measurement operation is provided along with information that the system is in the first operating state with continuous measuring operation.

4. The method in accordance with claim 2, wherein the set of measured values of the gas sensor is analyzed by the control unit in the fourth operating state and a sensor response is divided into a rise phase of the measured value, a measured value plateau phase and a fall phase of the measured value as the at least one characteristic variable to select the indicator of readiness for measurement operation of the gas sensor in the gas-measuring system and/or of the gas-measuring system.

5. The method in accordance with claim 2, wherein a peak of an amplitude of a measured signal of the gas sensor is analyzed by the control unit in the fourth operating state, as the at least one characteristic variable to determine the indicator of readiness for measurement operation of the gas sensor in the gas-measuring system and/or of the gas-measuring system, compared to an expected or predefined desired peak amplitude as the comparison variable.

6. The method in accordance with claim 2, wherein an average amplitude of a measured signal of the gas sensor is analyzed by the control unit in the fourth operating state, as the at least one characteristic variable to determine the indicator of readiness for measurement operation of the gas sensor in the gas-measuring system and/or of the gas-measuring system, compared to an expected or predefined average desired amplitude as the comparison variable.

7. The method in accordance with claim 2, wherein a duration of rise of a sensor response of a measured signal of the gas sensor is analyzed by the control unit in the fourth operating state, as the at least one characteristic variable to determine the indicator of readiness for measurement operation of the gas sensor in the gas-measuring system and/or of the gas-measuring system, compared to an expected or predefined duration of rise of the sensor response as the comparison variable.

8. The method in accordance with claim 2, wherein a gradient of rise of a measured signal of the gas sensor is analyzed by the control unit in the fourth operating state, as the at least one characteristic variable for determining the indicator of readiness for measurement operation of the gas sensor in the gas-measuring system and/or of the gas-measuring system, as a change in an amplitude of the measured value as a function of the time difference compared to an expected or predefined desired gradient of rise desired as the comparison variable.

9. The method in accordance with claim 2, wherein an integral of an amplitude of a measured signal of a sensor response of the gas sensor is analyzed by the control unit in the fourth operating state, as the at least one characteristic variable to determine the indicator of readiness for measurement operation of the gas sensor in the gas-measuring system and/or of the gas-measuring system, compared to an expected or predefined measured signal integral as the comparison variable.

10. The method in accordance with claim 2, wherein a duration of a sensor response of the measured signal of the gas sensor is analyzed by the control unit in the fourth operating state, as the at least one characteristic variable for determining the indicator of readiness for measurement operation of the gas sensor in the gas-measuring system and/or of the gas-measuring system, compared to an activation time of the test gas source as the comparison variable.

11. The method in accordance with claim 2, wherein in the fourth operating state the control unit analyses at least any two of the following as the at least one characteristic variable:
- a peak of an amplitude of a measured signal of the gas sensor compared to an expected or predefined desired peak amplitude as the comparison variable;
- an average amplitude of a measured signal of the gas sensor compared to an expected or predefined average desired amplitude as the comparison variable;
- a duration of rise of a sensor response of a measured signal of the gas sensor compared to an expected or predefined duration of rise of the sensor response as the comparison variable;
- a gradient of rise of a measured signal of the gas sensor as a change in an amplitude of the measured value as a function of the time difference compared to an expected or predefined desired gradient of rise desired as the comparison variable;
- an integral of an amplitude of a measured signal of a sensor response of the gas sensor compared to an expected or predefined measured signal integral as the comparison variable; and
- a duration of a sensor response of the measured signal of the gas sensor compared to an activation time of the test gas source as the comparison variable.

12. A gas-measuring system for monitoring gas of a measuring environment at which the gas-measuring system is situated, the gas-measuring system comprising:
- a gas sensor;
- a pumping device;
- a test gas source generating or providing a known test gas; and
- a control unit selecting an indicator of readiness for measurement operation of the gas sensor and/or of readiness for measurement operation of the gas-measuring system, the control unit being configured to coordinate a sequence of operating states comprising:
  controlling a continuous feeding of a predefined quantity of a gas or of a gas mixture, with the pumping device, from the measuring environment to the gas sensor to provide a continuous environmental gas measuring operation in a first operating state;
  reducing the quantity of gas fed by the pumping device to the gas sensor such that the feed of gas from the measuring environment is terminated in a second operating state;
  activating the test gas source in a third operating state to generate or provide the known test gas, with the feed of gas from the measuring environment terminated, in the third operating state;
  increasing the quantity of gas fed by the pumping device to the gas sensor to feed the test gas generated or provided by the test gas source to the gas sensor in the third operating state;
  deactivating the test gas source, after the end of the predefined time, in a fourth operating state;
  determining, by measurement with the gas sensor, the gas being fed to the gas sensor by the pumping device in the fourth operating state and recording a set of measured values over a time period;
  determining at least one characteristic variable from the set of measured values in the fourth operating state;
  selecting the indicator of readiness for measurement operation of the gas sensor in the gas-measuring system and/or of the gas-measuring system based on the at least one characteristic variable in the fourth operating state; and
  resuming the first operating state, with continuous measuring operation with continuous feeding of the predefined quantity of gas or gas mixture from the measuring environment through the pumping device from the fourth operating state whereby the indicator of readiness for measurement operation is selected and available with the system in the first operating state with ongoing continuous measuring operation.

13. The gas-measuring system in accordance with claim 12, further comprising data storage associated with the control unit providing saved data comprised of expected predefined comparison variables and providing saved data comprised of sensor states with each sensor state of the sensor states associated with one or more of the expected predefined comparison variables, wherein the control unit selects the indicator of readiness for measurement operation of the gas sensor in the gas-measuring system and/or of the gas-measuring system, by comparing the determined at least one characteristic variable with the list of expected predefined comparison variables and selects, based on the comparison and based on the association, one or more sensor states of the sensor states.

14. The gas-measuring system in accordance with claim 13, further comprising:

an output unit connected to the control unit, wherein a set of messages, each of the messages being associated with one or more of the sensor states, is provided by the output unit and is generated by the control unit or by the output unit connected to the control unit, which selects one or more sensor states of the list of sensor states including selecting one or more of the messages, in a fifth or in an additional operating state, on a basis of the indicator of readiness for measurement operation of the gas sensor, whereby the indicator of readiness for measurement operation is provided with information that the system is in the first operating state during continuous measuring operation.

15. The gas-measuring system in accordance with claim 13, wherein the set of measured values of the gas sensor is analyzed by the control unit in the fourth operating state and a sensor response is divided into a rise phase of the measured value, a measured value plateau phase and a fall phase of the measured value as the at least one characteristic variable to determine the indicator of readiness for measurement operation of the gas sensor in the gas-measuring system and/or of the gas-measuring system.

16. The gas-measuring system in accordance with claim 13, wherein a peak of an amplitude of a measured signal of the gas sensor is analyzed by the control unit in the fourth operating state, as the at least one characteristic variable to determine the indicator of readiness for measurement operation of the gas sensor in the gas-measuring system and/or of the gas-measuring system, compared to an expected or predefined desired peak amplitude as the comparison variable.

17. The gas-measuring system in accordance with claim 13, wherein an average amplitude of a measured signal of the gas sensor is analyzed by the control unit in the fourth operating state, as the at least one characteristic variable to determine the indicator of readiness for measurement operation of the gas sensor in the gas-measuring system and/or of the gas-measuring system, compared to an expected or predefined average desired amplitude as the comparison variable.

18. The gas-measuring system in accordance with claim 13, wherein a duration of rise of a sensor response of a measured signal of the gas sensor is analyzed by the control unit in the fourth operating state, as the at least one characteristic variable to determine the indicator of readiness for measurement operation of the gas sensor in the gas-measuring system and/or of the gas-measuring system, compared to an expected or predefined duration of rise of the sensor response as the comparison variable.

19. The gas-measuring system in accordance with claim 13, wherein a gradient of rise of a measured signal of the gas sensor is analyzed by the control unit in the fourth operating state, as the at least one characteristic variable for determining the indicator of readiness for measurement operation of the gas sensor in the gas-measuring system and/or of the gas-measuring system, as a change in an amplitude of the measured value as a function of the time difference compared to an expected or predefined desired gradient of rise desired as the comparison variable.

20. The gas-measuring system in accordance with claim 13, wherein an integral of an amplitude of a measured signal of a sensor response of the gas sensor is analyzed by the control unit in the fourth operating state, as the at least one characteristic variable to determine the indicator of readiness for measurement operation of the gas sensor in the gas-measuring system and/or of the gas-measuring system, compared to an expected or predefined measured signal integral as the comparison variable.

21. The gas-measuring system in accordance with claim 13, wherein a duration of a sensor response of the measured signal of the gas sensor is analyzed by the control unit in the fourth operating state, as the at least one characteristic variable for determining the indicator of readiness for measurement operation of the gas sensor in the gas-measuring system and/or of the gas-measuring system, compared to an activation time of the test gas source as the comparison variable.

22. The gas-measuring system in accordance with claim 13, wherein in the fourth operating state the control unit analyses at least any two of the following as the at least one characteristic variable:
- a peak of an amplitude of a measured signal of the gas sensor compared to an expected or predefined desired peak amplitude as the comparison variable;
- an average amplitude of a measured signal of the gas sensor compared to an expected or predefined average desired amplitude as the comparison variable;
- a duration of rise of a sensor response of a measured signal of the gas sensor compared to an expected or predefined duration of rise of the sensor response as the comparison variable;
- a gradient of rise of a measured signal of the gas sensor as a change in an amplitude of the measured value as a function of the time difference compared to an expected or predefined desired gradient of rise desired as the comparison variable;
- an integral of an amplitude of a measured signal of a sensor response of the gas sensor compared to an expected or predefined measured signal integral as the comparison variable; and
- a duration of a sensor response of the measured signal of the gas sensor compared to an activation time of the test gas source as the comparison variable.

* * * * *